United States Patent [19]

Arai et al.

[11] 4,332,258
[45] Jun. 1, 1982

[54] PORTABLE PULSE METER

[76] Inventors: Asajiro Arai; Yasuo Ugai, both c/o Kabushiki Kaisha Yamaoka Seisakusho, 93, Yokomichi, Hirakawa, Joyo, Kyoto, Japan

[21] Appl. No.: 191,706

[22] Filed: Sep. 29, 1980

[51] Int. Cl.³ .............................................. A61B 5/02
[52] U.S. Cl. .................................... 128/666; 128/687
[58] Field of Search ............................... 128/666, 687

[56] References Cited

U.S. PATENT DOCUMENTS

| 3,556,084 | 1/1971 | Budde | 128/666 |
| 3,796,213 | 3/1974 | Stephens | 128/666 |
| 3,810,460 | 5/1974 | Vannie | 128/666 |
| 3,841,314 | 10/1974 | Page | 128/666 |
| 4,129,124 | 12/1978 | Thalmann | 128/666 |

FOREIGN PATENT DOCUMENTS 2296396 7/1976 France .............................. 128/666

Primary Examiner—Robert W. Michell
Assistant Examiner—Francis J. Jaworski
Attorney, Agent, or Firm—Christensen, O'Connor, Johnson & Kindness

[57] ABSTRACT

A portable pulse meter comprising a rigid body, a detector plate provided with a light source and a photoelectric element for detecting the light from said source as reflected by a blood stream in a blood vessel, and means for resiliently mounting said detector plate on said rigid body so that said detector plate is movable relative to said rigid body.

6 Claims, 4 Drawing Figures

PORTABLE PULSE METER

This invention relates to a portable pulse meter.

The portable pulse meter is useful for measuring the pulse of a person who is taking physical exercise such as running a marathon. The pulse of a person can be detected by detecting a blood stream through a blood vessel. For detection of blood stream a light source is so arranged as to project light onto a portion of the surface of the skin of a person to be examined. The projected light passes through the skin to impinge on a blood vessel to be reflected thereby, and a photoelectric element is so arranged as to detect the reflected light.

The intensity of the reflected light is different when the projected light hits a blood stream from when it does not. Therefore, by detecting the output produced by the photoelectric element when it has detected the reflected light, it is possible to measure the pulse. Practically, the output signal from the photoelectric element caused by the light reflected by blood stream is measured for a unit period of time.

A portable pulse meter is conveniently mounted on a finger of a hand of a person to be examined so that the instrument is not obstructive to physical exercise. To this end a light source and a photoelectric element are mounted on a detector plate, which may be worn by a finger of a hand of a person to be examined.

As can be easily understood from the above-mentioned principle of pulse measurement, the relative position between the detector plate having a light source and a photoelectric element mounted thereon and the finger carrying the detector plate must be fixed. Otherwise, the photoelectric element could not receive the light reflected by the same portion of a blood vessel, and the amplitude of the output pulse from the element would fluctuate. Moreover, if the above-mentioned relative position is unstable, noise would be produced so as to be superimposed on the output pulse of the photoelectric element, so that it would be impossible to detect the pulse accurately.

The finger and the detector plate must always be kept in contact with each other with a constant pressure. If the pressure is too high, the detector plate squeezes the blood vessel to stop the blood stream therethrough. If the pressure is too low, the relative position between the detector plate and the finger is likely to change.

Accordingly, the primary object of the invention is to enable accurate detection of the pulse.

Another object of the invention is to provide an improved pulse meter wherein the relative position between the detector plate and the portion of the skin on which the detector plate is attached is fixed and stable.

Another object of the invention is to provide such a pulse meter as aforesaid wherein the detector plate and the finger can be kept in contact with each other with a suitable pressure.

In accordance with the invention, the detector plate on which a light source and a photoelectric element are mounted is resiliently suspended from the body of the instrument by means of springs. Without any finger contacting with the detector plate, the forces of the springs balance to keep the detector plate stationary. When a finger tip is applied to the detector plate to press it down to a required position, the resiliency of the springs counteracts and balances the pressure exercised by the finger tip so that the pressure between the finger tip and the detector plate is kept at a constant value.

When the finger tip moves laterally, the detector plate is moved by the movement of the finger tip against the force of the springs, so that the relative position of the finger tip to the detector plate is kept unchanged despite the movement of the finger tip.

The invention will be described further in detail with reference to the accompanying drawings, wherein.

Figures 1, 2, 3, 4:
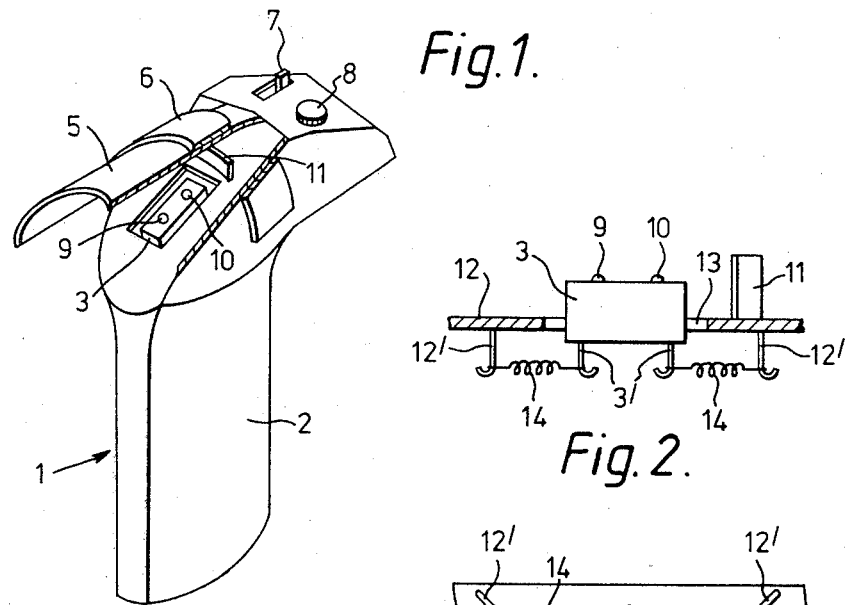
FIG. 1 is a perspective view, partly cut away, of one embodiment of the invention.
FIG. 2 is a sectional view of a portion of FIG. 1.
FIG. 3 is a bottom view of FIG. 2.
FIG. 4 is a view similar to FIG. 2 with a finger tip shown pressing the detector plate.

In FIG. 1, there is shown a pulse meter comprising a body 1 so shaped as to be easily gripped by the hand of a person to be examined. In particular, the body 1 has a grip 2 so shaped as to be held conveniently by the palm and the four fingers other than the thumb of a human hand.

The grip 2 encloses the components of necessary electrical circuits such as a circuit for amplifying the pulses, and other elements.

The body 1 is provided with an upper mounting plate 12 having a square opening 13 formed therein. A detector plate 3 is suspended from the plate 12 by means of four coil springs 14 so as to be positioned in the opening 13.

On the upper surface of the detector plate 3 there are provided a light source 9 such as a light-emitting diode which produces near-infrared rays and a photoelectric element 10 such as a phototransistor which detects the light from the source 9.

Each of the four coil springs 14 has its one end fixed to the mounting plate 12 adjacent the periphery of the opening 13 as at 12' and the opposite end fixed to the bottom of the detector 3 as at 3'.

While the pulse meter is inoperative, the detector plate 3 remains stationary at a position where the weight of the detector plate 3 balances the forces of the springs 14. At this position the upper surface of the detector plate 3 is at the same level as or a little above the upper surface of the mounting plate 12.

When a person to be examined applies the inner side of the finger tip of one of his or her fingers, usually, the thumb 4 onto the upper surface of the detector plate 3, with the position of the finger tip being guided by a stopper 11, the detector plate 3 is pressed down against the forces of the springs 14 as far as it is held stationary at a position where the pressure by the finger tip is balanced by the forces of the springs 14.

To bind the finger tip at the position, a band 6 is provided to bind the finger tip, with a cover 5 laid over the finger tip thereby to shelter the photoelectric element 10 from external light, so that the element 10 may not be excited by external light.

In the illustrated embodiment, the band 6 is placed on the outer surface of the cover 5 to bind the finger tip from outside the cover. Alternatively, the band 6 may be placed inside the cover so as to bind the finger directly.

The body 1 of the pulse meter may be provided with a knob 7 of a switch (not shown) for controlling a source of electricity and a dial 8 for controlling a variable resistor (not shown) for adjustment of sensitivity.

As previously mentioned, the finger tip 4 of the hand of a person to be examined is applied onto the surface of the mounting plate 12 and then fixed by binding with the band 6, so that the detector plate 3 is pressed downward by the finger tip 4 as far as the pressure balances the forces of the springs 14, whereupon the pressure between the detector plate 3 and the finger tip 4 is kept substantially constant.

Even with the band 6 restricting the finger tip 4, it is unavoidable that the finger tip 4 moves more or less. However, even if the finger tip 4 moves back and forth or right and left, since the detector plate 3 is suspended by the springs 14, the detector plate 3 follows the movement of the finger tip 4 within the opening 13 so that the relative position of the finger tip 4 and the detector plate 3 is kept substantially unchanged. If the finger tip moves up and down, the resiliency of the springs 14 allows the detector plate 3 to follow the movement of the finger tip so that the relative position of the finger tip and the detector plate 3 also is kept unchanged in this case.

In the illustrated embodiment, four springs are used to suspend the detector plate 3 in such a manner that they pull the detector plate 3 in four radial directions. Instead of the four springs two springs may be provided one at each of the opposite sides of the detector so that they pull the detector plate 3 in opposite directions. Five or more springs may be used if required.

Instead of the coil springs used in the illustrated embodiment, leaf springs may also be used.

What we claim is:

1. A portable physiological pulse meter comprising a rigid body, a detector plate provided with a light source and a photoelectric element for detecting the light from said source as reflected by a blood stream in a blood vessel in a portion of human anatomy brought into proximity with said detector plate, and means for resiliently mounting said detector plate on said rigid body so that said detector plate is omnidirectionally movable relative to said body so as to minimize relative movement between said detector plate and said portion of said human anatomy, thereby minimizing measurement noise.

2. The device of claim 1, wherein said mounting means comprises springs.

3. The device of claim 2, wherein said detector plate is rectangular and said springs suspend said detector plate at the four corners thereof.

4. The device of claim 1, wherein said rigid body comprises a mounting plate having an opening in which said detector plate is disposed, said opening being larger than the exterior dimensions of said detector plate to permit lateral movement of said detector plate within said opening.

5. The device of claim 1, further including means provided above said detector plate for binding that portion of a human body onto which said device is to be mounted.

6. The device of claim 1, further including a cover provided above said detector plate for covering the portion of a human body to be examined thereby to prevent said photoelectric element from detecting external light.

* * * * *